US011331479B2

(12) United States Patent
Kjeken et al.

(10) Patent No.: US 11,331,479 B2
(45) Date of Patent: May 17, 2022

(54) DEVICE AND METHOD FOR SINGLE-NEEDLE IN VIVO ELECTROPORATION

(71) Applicant: Inovio Pharmaceuticals, Inc., Plymouth Meeting, PA (US)

(72) Inventors: Rune Kjeken, San Diego, CA (US); Iacob Mathiesen, San Diego, CA (US); Elisabeth Torunn Tjelle, San Diego, CA (US); George McHugh, San Diego, CA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 104 days.

(21) Appl. No.: 16/506,888

(22) Filed: Jul. 9, 2019

(65) Prior Publication Data

US 2020/0001076 A1    Jan. 2, 2020

Related U.S. Application Data

(62) Division of application No. 11/704,591, filed on Feb. 9, 2007, now Pat. No. 10,369,359.
(Continued)

(51) Int. Cl.
*A61N 1/32* (2006.01)
*A61N 1/30* (2006.01)

(52) U.S. Cl.
CPC ............... *A61N 1/327* (2013.01); *A61N 1/30* (2013.01)

(58) Field of Classification Search
CPC ........ A61N 1/327; A61N 1/30; A61N 1/0412; A61N 1/0416; A61N 1/042; A61N 1/0424;
(Continued)

(56) References Cited

U.S. PATENT DOCUMENTS

| 3,313,293 A | 4/1967 | Chesebrough et al. |
| 5,019,034 A | 5/1991 | Weaver et al. |

(Continued)

FOREIGN PATENT DOCUMENTS

| JP | 4-158870 A | 6/1992 |
| WO | 01/43817 A1 | 6/2001 |

(Continued)

OTHER PUBLICATIONS

Lee et al., "Surfactant-Induced Sealing of Electropermeabilized Skeletal Muscle Membranes In Vivo", Proc. Natl. Acad. Sci. USA, 89(10):4524-1528 (1992) [Cited in related U.S. Appl. No. 11/704,591].
(Continued)

*Primary Examiner* — Scott J Medway
*Assistant Examiner* — John A Doubrava
(74) *Attorney, Agent, or Firm* — BakerHostetler

(57) ABSTRACT

Described is a device and method for administration of molecules to tissue in vivo for various medical applications, the device comprising a single hypodermic injection needle and at least two spaced elongate electrodes which provide for the ability, when the needle is inserted into tissue, such as skin or muscle, to pulse tissue with a non-uniform electric field sufficient to cause reversible poration of cells lying along or in close proximity to the track made by the needle upon its insertion into said tissue.

15 Claims, 19 Drawing Sheets

Related U.S. Application Data

(60) Provisional application No. 60/772,255, filed on Feb. 11, 2006.

(58) Field of Classification Search
CPC .......... A61N 1/0502; A61M 2205/054; A61M 2205/055; A61M 2037/0023; A61M 2037/003; A61B 2018/00613
See application file for complete search history.

(56) References Cited

U.S. PATENT DOCUMENTS

| | | | |
|---|---|---|---|
| 5,273,525 A * | 12/1993 | Hofmann | A61N 1/327 604/21 |
| 5,328,451 A * | 7/1994 | Davis | A61N 1/306 422/22 |
| 5,389,069 A | 2/1995 | Weaver | |
| 5,702,359 A | 12/1997 | Hofmann et al. | |
| 5,830,663 A | 11/1998 | Embleton et al. | |
| 5,873,849 A * | 2/1999 | Bernard | A61N 1/326 604/20 |
| 6,119,037 A | 9/2000 | Kellogg et al. | |
| 6,135,990 A | 10/2000 | Heller et al. | |
| 6,181,964 B1 | 1/2001 | Hofmann et al. | |
| 6,356,783 B1 | 3/2002 | Hubbard, Jr. | |
| 6,451,002 B1 * | 9/2002 | Dev | A61N 1/325 604/500 |
| 6,485,488 B1 | 11/2002 | Muller et al. | |
| 6,591,133 B1 | 7/2003 | Joshi | |
| 6,603,998 B1 | 8/2003 | King et al. | |
| 6,623,515 B2 | 9/2003 | Mulier et al. | |
| 6,778,853 B1 | 8/2004 | Heller et al. | |
| 6,993,348 B2 | 1/2006 | Ikegami et al. | |
| 7,127,284 B2 | 10/2006 | Seward | |
| 7,294,126 B2 | 11/2007 | Sampson et al. | |
| 7,328,064 B2 | 2/2008 | Mathiesen et al. | |
| 7,776,373 B2 * | 8/2010 | Pelletier | A23L 5/30 426/237 |
| 8,209,006 B2 * | 6/2012 | Smith | A61N 1/0412 604/21 |
| 2002/0198512 A1 | 12/2002 | Seward | |
| 2003/0060856 A1 | 3/2003 | Chornenky et al. | |
| 2003/0073238 A1 * | 4/2003 | Dzekunov | A61K 48/0091 435/461 |
| 2005/0070841 A1 | 3/2005 | Mathiesen et al. | |
| 2005/0123565 A1 | 6/2005 | Subramony et al. | |
| 2005/0209548 A1 * | 9/2005 | Dev | A61N 1/306 604/20 |
| 2006/0089674 A1 | 4/2006 | Walters et al. | |
| 2006/0293725 A1 | 12/2006 | Rubinsky et al. | |
| 2007/0083239 A1 | 4/2007 | Demarais et al. | |
| 2008/0045880 A1 | 2/2008 | Kjeken et al. | |
| 2009/0219647 A1 | 9/2009 | Hunt et al. | |

FOREIGN PATENT DOCUMENTS

| | | |
|---|---|---|
| WO | 03/075978 A2 | 9/2003 |
| WO | 2004/000825 A1 | 12/2003 |
| WO | 2004004825 A2 | 1/2004 |
| WO | 2004066903 A2 | 8/2004 |

OTHER PUBLICATIONS

Cheng et al., "Use of Green Fluorescent Protein Variants to Monitor Gene Transfer and Expression in Mammalian Cells", Nature Biotechnology 14(5):608-9 (1996) [Cited in related U.S. Appl. No. 11/704,591].

* cited by examiner

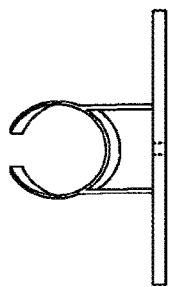
*Fig. 9C*
*Fig. 9D*
FRONT
BACK
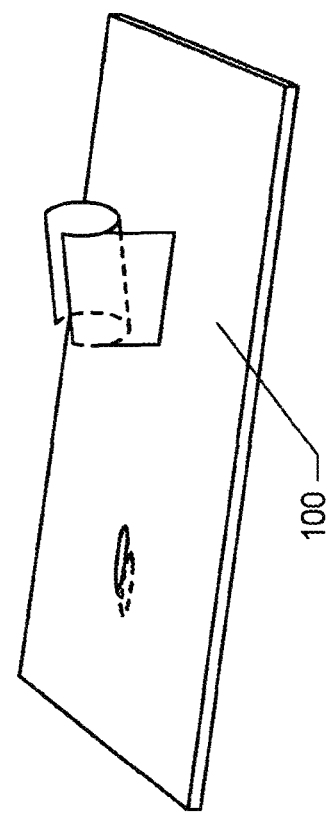
*Fig. 9B*
100
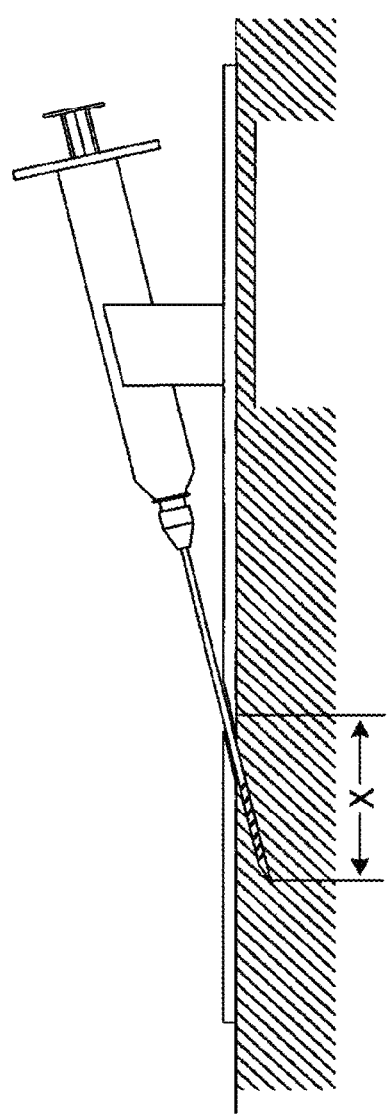
*Fig. 9A*
X

DEVICE AND METHOD FOR SINGLE-NEEDLE IN VIVO ELECTROPORATION

CROSS REFERENCE TO RELATED APPLICATIONS

This application is a divisional application of U.S. patent application Ser. No. 11/704,591, filed Feb. 9, 2007, which claims the benefit of Provisional Application No. 60/772,255, filed Feb. 11, 2006 the entirety of which is incorporated by reference.

TECHNICAL FIELD

This invention relates to electroporation of cells in vivo, particularly cells of a patient's tissues. More specifically, this invention relates to novel devices and methods for delivering molecules to cells situated at, near and/or adjacent to a predetermined insertion track site of an elongate single-needle electrode. Still more specifically, the invention concerns the electroporated delivery of substances into cells along and in the vicinity of the needle track made by insertion of the electrode from the surface of a tissue and into the tissue to a depth of from 3 millimeters to 3 cm, which tissues can comprise any tissues, including without limitation skin, striated and smooth muscle, mucosa, and organs.

BACKGROUND

The following description includes information that may be useful in understanding the present invention. It is not an admission that any such information is prior art, or relevant, to the presently claimed inventions, or that any publication specifically or implicitly referenced is prior art.

Electroporation has been applied to delivering molecules to subsurface tissues using various multiple-electrode designs such as arrays of two or more electrodes that typically are designed as needle electrodes for insertion into said tissue. Generally, such arrays define a treatment zone lying between the needle electrodes of the array. Such treatment zones therefore comprise a three dimensional volume of tissue wherein cells within the treatment zone are exposed to an electric field of an intensity sufficient to cause temporary or reversible poration, or even sometimes irreversible poration, of the cell membranes to those cells lying within and or near the three dimensional volume.

Current practices for electroporating cells in tissue include use of significant voltages in order to impart through the three dimensional treatment zone a relatively uniform electric field. By "relatively uniform" is meant that electric lines of force coincident with application of an electric pulse sufficient to cause poration is imparted across the cells somewhat evenly throughout the three dimensional treatment zone volume. Ultimately, a large number of electrode needles combined with large injection volumes and high electrical fields have been necessary to ensure a sufficient overlap between an injected drug and the tissue volume experiencing the electrical field since typically, the injection bolus that is delivered to the tissues quickly spreads from the injection site. Use of high electric fields and large electrode arrays has several drawbacks. For example, use of many needles and high electric field (voltages) causes more pain while high injection volume makes dosing difficult to control as it causes waste of the drug (most of the drug is not getting into the cells as it will be outside the treatment zone). Also, use of such multiple needle devices is cumbersome and a cause for apprehension from the standpoint of the patient.

Besides the invasive aspect of a device with multiple needles, typical electroporation techniques, as stated above, result in variability in electroporation of cells within a treatment zone. This is a drawback to medical use of electroporation in that dispersion of treatment molecules of the injected bolus into surrounding tissue results in loss of control as to the amount of such treatment molecule that is ultimately transfected into cells within the treatment zone by the electroporation event. Thus, a need exists in the electroporation arts for a device and method to narrow or refine control over "dosing" of treatment molecules into specific and well defined delivery sites within a patient's tissue. Likewise, there is still a need in the art for methodologies and devices that can electroporate with less invasiveness and impart less pain from the electric field pulse employed in the delivery of therapeutic substances to various tissues including skin, muscle, mucosa and organs.

SUMMARY

In a first embodiment, this invention provides for electroporation of cells in situ, particularly cells that are located subcutaneously, intradermally, subdermally, and/or intramuscularly (particularly skeletal muscle, striated, and smooth muscle, e.g., heart, muscle). In a related embodiment, the invention provides for the electroporation of cells near and/or adjacent to the track made by insertion of the single elongate needle electrode into tissue. For example, cells that become electroporated using the invention device are those situated within a radius from the needle track anywhere from between 0.0 and 5 mm so as to comprise a generally cylindrical treatment zone imparted by the novel design and pulsing of and of the electric field imparted into the tissue by the single-needle electrode.

In a second embodiment, the invention provides for any number of structural arrangements providing for at least two opposite electrode leads (i.e., at least one anode and at least one cathode) situated in association with a single elongate electrically inert shaft, which shaft itself can comprise electrodes and an electrically inert material, such as a medically acceptable plastic or polycarbonate, filling the space between the electrodes a 0.05 mm to a 1.5 mm between, or can comprise just elongate opposing spaced electrodes. In either embodiment, the electrodes of the tissue penetrating single needle electrode or electrode containing shaft have spaced dimensions of between 0.05 mm and 1.5 mm. In a related embodiment, the electrodes themselves can have a length exposed along the elongate shaft anywhere from the whole needle length to just a section of the needle, such as near the shaft penetration tip. Further, the electrodes can have cross sectional dimensions of between 0.005 and 0.80 mm. In yet another structural arrangement embodiment, the single needle electrode can comprise a hypodermic needle comprising at least two elongate electrodes spaced along at least a portion of the length of the hypodermic needle exterior. For example, the hypodermic needle can include at least two electrodes (i.e., an anode and a cathode) running along a portion of the length of the needle. (See FIG. 1.) In working embodiments, each electrode is connected to a source of electric energy for generating an electric field between opposite poles, i.e., one electrode is an anode and the other a cathode electrode. In other examples, multiple electrodes can be formed on the exterior of a hypodermic injection needle such as disclosed in FIG. 3A comprising multiple straight and parallel electrodes, or as depicted in FIGS. 2 and 4 comprising multiple electrodes spiraled around the injection needle. In still further embodiments, the single-needle electrodes can be manufactured using any number of well understood methods including etching and layering per Micro electro-mechanical systems (MEMS) technologies. In such manufacturing methods, micromachining processes are used to add or strip away layers of substances important to the proper annealing, insulation, and conduct of electric pulses and circuitry. FIGS. 13A, B, C, D and E are photographs of the embodiment wherein the electrodes are etched on to the delivery needle shaft. Specifically, gold electrode layering has been coated above a layer of and inert substance (parylene) which itself had been layered over the hypodermic needle shaft. Additional methods for manufacturing the elongate electrodes include extrusion technologies wherein the electrode leads are formed into and or along the shaft of an electrically inert composition having insulating qualities, such a plastic, a polyester derivative, or polyvinylchloride (PVC), or insulative carbon fiber. As shown in FIGS. 14 A and B, an elongate hollow needle can be extruded with electrode component, such as for example, wire either along opposite sides of the hollow shaft or in a spiral fashion as shown in FIG. 14 B. Further still, the needle shaft can also comprise sections with no exposed electrodes. For example, one end of the needle shaft connects to a hub forming a connector for connecting to a source of fluid, such as for example, a syringe. Insulation near or along such section of the shaft may provide for additional lessening of electric stimulus sensation noticeable by the patient. In yet a further embodiment with respect to any such electrode configuration described herein, each of the electrodes are individually energizable so that any combination of the electrodes may be energized in pairs (i.e., a cathode and anode) simultaneously together, or in any given sequence, and further using any type of pulse including without limitation monopolar, bipolar, exponential decaying, or pulse train combinations of any of the former.

In a third embodiment, the invention provides for use of relatively low voltage and/or low current, which in turn not only provides sufficient electrical energy for causing reversible poration of cells in the treatment zone, but also allows for a low pain level experienced by subjects during application of electric pulses into the surrounding tissue, said application using nominal electric field strengths of generally between 1 and 100 V, typically between 2 and 50V, an more preferably between 3 and 25V. In a related aspect, electric current employed in the invention device and methods uses generally between 1-400 mAmps, typically between 5-200 mAmps, and more preferably between 20 and 100 mAmps. In a related embodiment, the amperage chosen depends on the total surface area of the electrodes. For example, the device may employ a range between 10 to 40, or 25 to 100, or 50 to 150, or 125 to 200, or 175 to 250, or 225 to 300, or 250 to 300 or 300 to 400 mAmps depending upon the total electrode surface area of each electrode. The smaller the surface area, the lower the amperage necessary to achieve an electroporating electric filed in the in situ tissue. Pulses can be applied for between 1 and 1000 millisec.

In another embodiment, the invention provides for delivery of treatment molecules at various concentrations (e.g., for example, between 0.05 μg-3 mg/ml) and preferably at low bolus volumes (e.g., for example, generally 1 μl to 1 ml). In a related embodiment, using a structural embodiment inclusive of a delivery tube associated with the single needle electrode shaft, the volume of treatment molecules immediately following injection into the tissue (such as a controlled injection wherein the injectate is delivered during insertion of the needle) surprisingly remains to a substantial level in the vicinity of the injection needle track. Treatment molecules are contemplated to include therapeutic drugs, e.g., small molecules, organic compounds, as well as proteins, and nucleic acids encoding polypeptides having either a biologic activity or that will induce an immune response in the host once such polypeptide is expressed in the electroporated cell. The polypeptides once expressed in the cell are available for interacting with cellular metabolic machinery and immune system pathways.

In yet another embodiment, electrical energy used to pulse the tissue provides for a unique electric field that is unlike prior applied fields used for electroporation of similar tissues. Specifically, prior art electric fields intentionally and inherently impart what has been recognized in the electroporative arts as a "uniform" electric field meaning that the applied electrical energy is of sufficient strength to impart a nominal field strength and a relatively even voltage drop across the treatment zone created by widely separating the electrodes a given distance apart from one another and placing the target treatment zone optimally central between said spaced electrodes. Such electrode array designs when pulsed in tissue tend to electroporate cells primarily within the zone bordered by the electrodes generally in the vicinity of the electric lines of force and to a smaller degree a zone of cells situated just adjacent and surrounding the three dimensional treatment zone.

In contrast, the current invention uses electric fields that comprise a generally cylindrical or columnar "non-uniform" field that is created about the length of the needle shaft thereby creating a treatment zone of cells lying within an area close enough to the centrally placed electrodes to be subjected to an electroporation field "outside" the immediate location of the electrodes, of sufficient strength to porate said cells. Such a treatment zone is completely external to and surrounding the central needle and electrodes and the non-uniform field dissipates relative to the distance outward from the electrode/needle. Generally, it is thought that the dissipation in electrical energy as the distance from the single needle electrode increases is parallel to the dissipation found in other physical phenomenon wherein energy, here energy sufficient to reversibly porate cells, dissipates at an exponential rate. However, such dissipation rate if applicable does not negatively affect the functioning of the invention device or the intended outcome of delivering substances into cells in a defined zone. Thus, since electrical energy necessary to cause cell poration dissipates with the distance from the electrical field source, the area around the needle tract that is susceptible to electroporation is inherently confined to a central core correlating to the length of the needle track and laterally to a given radius forming therefore a generally cylindrical treatment zone of variable radii depending upon the pulse energy imparted to the electrodes. In a further related embodiment, the more energy used to pulse, the greater the potential to damage cells directly in contact with the electrodes. It is yet a further intention of the invention methods to employ the ability to cause such damage for the purpose of further stimulating the immune system. Thus, treatment regimens can be used that intentionally impart a greater rather than a lesser energy so as to provide a stimulus for immune response activity around the treatment site.

In other embodiments, the device can be used to deliver drugs, natural polypeptides having a biologic activity, and genes encoding such polypeptides that can be expressed in situ in cells within the treatment zone for treating disorders or for modulating an immune response in the host and/or for treating a variety of diseases including but not limited to diseases caused by pathogenic organisms and viruses and cancers.

Other features and advantages of the invention will be apparent from the following drawings, detailed description, and appended claims.

BRIEF DESCRIPTION OF THE DRAWINGS

FIG. 8A shows three opposing electrodes in a linear array wherein the lines of force between the electrodes are relatively uniform. In FIGS. 8B and C is depicted circular arrays wherein the treatment zone is central to the electrodes and under relatively uniform lines of force and respective electric fields (individually pulsed in opposing pairs, FIG. 8B, or pulsed in pairs of opposing electrodes in different orientations, FIG. 8C).

FIGS. 9A-D show yet a further embodiment of the invention device which comprises a guide for resting the needle and reservoir for penetration of tissue to be treated at an acute angle for use in methods that include delivery of treatment substances near the tissue surface. This angle is typically between 3 and 25 degrees from the plane formed by the general area of the tissue surface.

FIG. 10A depicts a needle supporting straight electrodes while

In FIG. 11A is a series of photos showing adjacent slices of tissue while

FIG. 13A shows one view of the needle showing one long electrode running the length of the needle.

FIGS. 14 A, B, and C are drawings showing additional embodiments of single-needle design where in the shaft comprises electrically inert material such as for example, plastic extruded with electrode leads built into the extruded hypodermic shaft.

DETAILED DESCRIPTION OF ILLUSTRATIVE EMBODIMENTS

Figure 2:
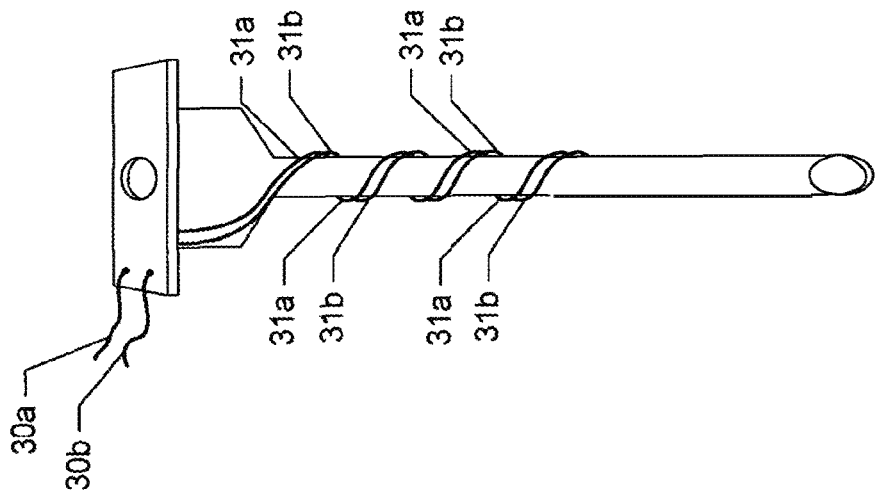
FIG. 2 depicts an alternate embodiment of the invention device wherein the anode and cathode electrodes are parallel to one another through a plane formed in a spiral around the needle.
Figure 4:
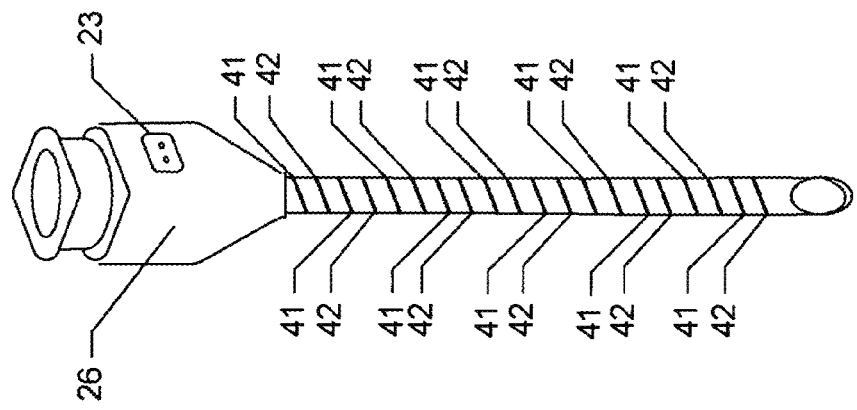
FIG. 4 is another example of an embodiment comprising electrodes spiraled around the delivery needle. The electrodes so spiraled can comprise a multiplicity of anode and cathode pairs, but typically comprise one or two pairs of electrodes, each pair comprising an anode and a cathode.
Figure 3B:
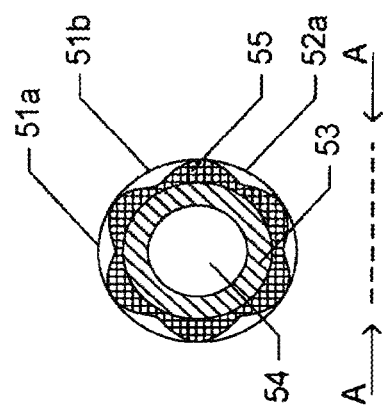
FIG. 3B depicts a view of the cross section of one example of an invention electrode along line A-A. As shown, in one configuration, the electrodes can be layered by any number of techniques known to those of skill in the fabrication arts on the outer sections of a delivery tube and lumen. In the drawing is depicted an inner needle 53 with lumen 54 surrounded by an insulating material 55 on which is layered the electrodes.
Figure 3A:
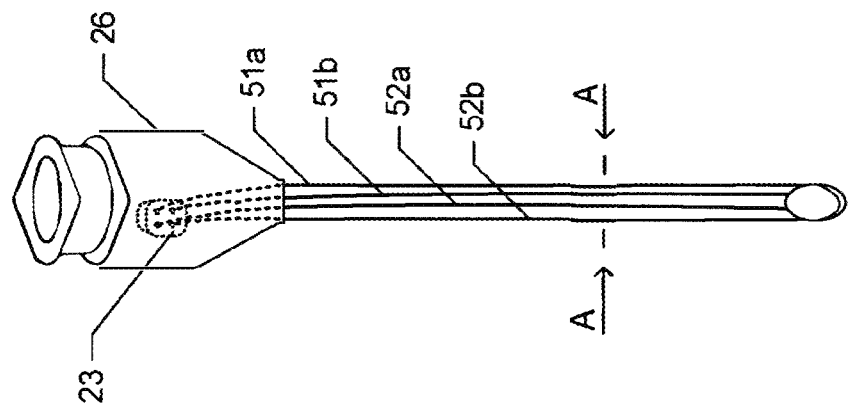
FIG. 3A is another alternate embodiment wherein a delivery needle comprises a multiplicity of anode and cathode electrodes running straight and parallel along the length of the delivery needle. As also depicted, this figure includes an example of a connector for connecting the electrodes to a source of electrical energy.

In a first embodiment, the invention comprises a device for electroporation of tissue in vivo comprising a hollow shaft made of a material capable of insertion into a biologic tissue or organ in situ and of delivering therethrough a fluid medium (i.e., a delivery needle shaft), said shaft further comprising at least two electrodes exposed at least in part on an outer surface of said shaft, wherein said electrodes are spaced from one another and situated parallel with respect to one another along said needle shaft. Embodiments for electrodes can employ a variety of electrode structural designs. For example, anode and cathode electrodes can be electrically isolated from one another, placed in association with a delivery needle that run parallel to one-another and to the length of the delivery needle such as disclosed in FIGS. 1 and 3A, or that are parallel to each other but are spiraled around the needle shaft as depicted in FIGS. 2 and 4. The invention device also includes electric conduits connecting each of said electrodes to an electrical energy source wherein said electrodes when said needle is inserted into a patient tissue are capable of being energized individually, generating an electric field to cells in a treatment zone surrounding said needle sufficient to cause cells along and near a track made by insertion of said needle into said tissue to become reversibly porated so as to allow treatment molecules to enter said cells.

Figure 14B:
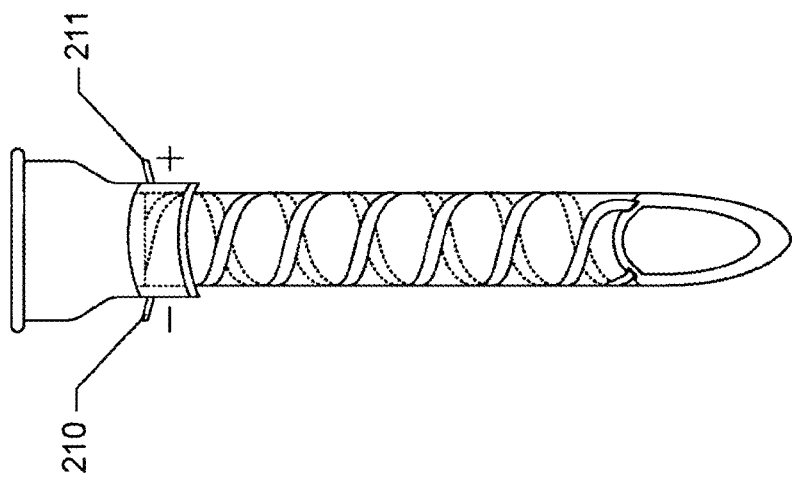
FIG. 14B depicts electrodes in a spiral about the shaft.
Figure 14C:
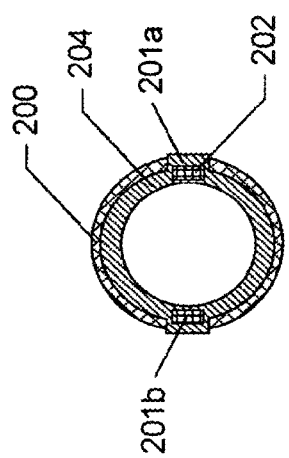
FIG. 14C depicts the cross section AA-AA of FIG. 14A showing one embodiment wherein the electrode of the shaft can be connected to electrode leads positioned on the needle hub.
Figure 14A:
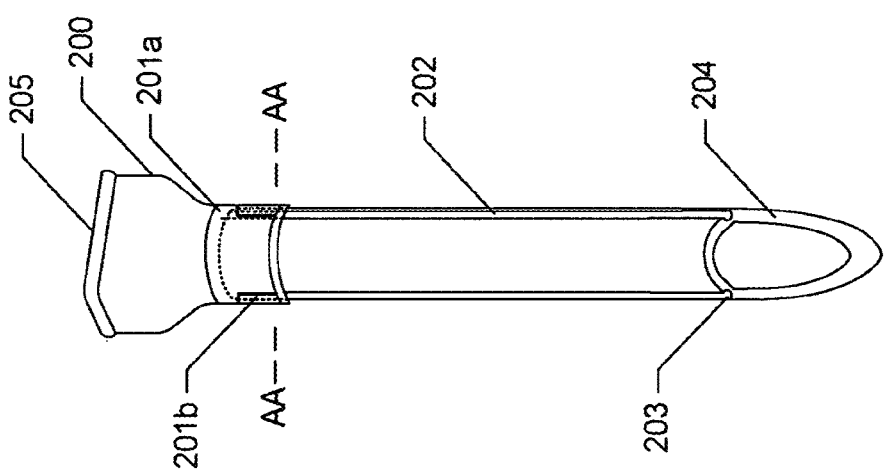
FIG. 14A depicts straight electrodes running parallel to the needle shaft.

Manufacture of such electrode containing fluid delivery needles can be carried out by any number of well know methods including micromachining such as commonly understood as MEMs technology. For example, a standard hypodermic needle (which can be any gauge such as 20 gauge, 21 gauge, 22 gauge, 23 gauge, 24 gauge, 25 gauge 26 gauge, 27 gauge, 28 gauge and 29 gauge) can be coated with an electrically inert material followed by deposition of electrically conductive material such as gold, followed in turn by etching away conductive material in the orientation desired on the surface of the needle. Specifically, generally the process comprises cleaning the hypodermic needle shaft in preparation for deposition of the inert substance, for example, a polymer having properties of evenly adhering to surfaces, such as parylene. Following stripping of the metal shaft, parylene is deposited, such as by vacuum deposition, on to the needle. This is in turn patterned using a laser to deposit electrode conductable material, such as gold, followed in turn by selective removal of the gold to form electrodes in a predetermined pattern on the needle shaft. In the current invention, the use of MEMs technology provides for an ability to manipulate the three dimensional needle and coatings and etchings on a miniature scale. The capability to manufacture a single needle electrode is proven by the photographs of FIGS. 13A to E. Manufacture can also be carried out by extrusion technology. As depicted in FIGS. 14A-C, in this aspect the electrodes 202 and 203 (FIG. 14A) are extruded as fine wire filaments with an electrically inert substance such as polyvinylchlorine or the like in a linear fashion. The tip of the needle 204 can be machined or cut to a penetrating tip and at the other end fitted to a hub 200 comprising electrode leads 201*a* and 201*b* and a fitting 205 for attachment to a source of fluid medium. FIG. 14B depicts an example of a structural embodiment comprising an extruded needle with spiral electrodes and electrode leads 210 and 211.

In a second embodiment, the invention comprises a method for delivering molecules to cells in vivo comprising providing to a patient's tissue containing said cells an injection needle further comprising at least two elongate electrodes (i.e., a cathode and an anode) positioned along the needle shaft and at least a reservoir containing said molecules wherein said reservoir and molecules are in fluid communication with a lumen running through said needle shaft, injecting the molecules into said tissue, and energizing the electrodes with electrical energy to provide an electric pulse sufficient to cause cells in the vicinity of the injection site and needle track to become reversibly porated, thereby electroporating said cells for their uptake of said molecules. The reservoir can have a variable volume capacity selected from 0.0 to 0.5 ml, 0.0 to 1 ml, 0.0 to 3 ml, and 0.0 to 5 ml.

In a third embodiment, the device provides for electroporation of cells in a narrowly defined location, particularly cells along or near the track make by the injection needle. Generally, the cells considered within the treatment site are those cells lying in a radius around the needle track of about 5 mm, more typically about 3 mm, and even more particularly about 2 mm, and most particularly about 1 mm. In a related embodiment, the generation of electric filed sufficient for electroporation of cells within said treatment site is a field that weakens outward from the central injection needle such that the treatment site is defined by the inability of the pulse energy to extend into the tissues beyond a certain distance from the electrodes.

In a further related embodiment, the invention calls for the novel use of a single elongate probe (which comprises the injection needle and electrodes) for performing in situ electroporation of a highly localized set of cells in the tissue.

In another embodiment, the invention device may be used with any of a variety of electric pulsing conditions. For example, the electrodes can be charged with at least one pulse of constant current in the range of between 1-400 mAmps, typically between 5-200 mAmps, and more preferably between 20 and 100 mAmps. In another example, the electrodes can be charged with a voltage pulse in the range of 1 to 100 volts. Further, the electric pulse can be either a monopolar or a bipolar pulse wherein said pulse can be a single, a double or a multiple pulse sequence having various characteristics such as a set voltage drop, variable shaped pulse trains, or pulses employing constant current. An electroporation pulse generator can be capable of generating electric pulses wherein the average voltage can range between 1 to 200 V. The generator is capable of generating electric pulses having a frequency from 1 to 10,000 Hz. The generator can be pulsed for a time length between about 0.1 us to 1000 ms.

In other embodiments, the device and method provide for delivering or transfecting pharmaceutical drugs, proteins, nucleic acids including DNA and RNA, and synthetic modifications thereof as are well known to those of skill in the art, into patient tissues, particular to cells residing in the subcutaneous, intradermal, and subdermal spaces as well as skeletal and striated muscle compartments of a mammalian body, breast and organs including heart, lung, pancreas, spleen, liver, and organs of the alimentary tract. Once transfected with the selected material, cells will be directly affected by the activity of the drug, or protein or nucleic acid. Where nucleic acids are transfected, typically such nucleic acids are employed for the protein encoded thereby which can be expressed in the cells of the treatment site. Further, the substances can comprise cytokines, chemokines, and immune relevant bioactive molecules including such active molecules as immune modulating molecules selected from the group consisting of IL-1, IL-2, IL-3, IL-4, IL-5, IL-6, IL-7, IL-8, IL-9, IL-10, IL-11, IL-12, GM-CSF, M-CSF, G-CSF, LIF, LT, TGF-β, IFN, TNF-α, BCGF, CD2, or ICAM.

In another embodiment, the material to be delivered to the cells can be delivered in a liquid form in a volume of between 0.01 ml to 1 ml. In one embodiment, nucleic acid encoding a polypeptide can be dissolved in 0.9% sodium chloride (NaCl). The exact solvent, however, is not critical to the invention. For example, it is well known in the art that other solvents such as sucrose are capable of increasing nucleic acid uptake in skeletal muscle. In a related embodiment, the volume to be delivered can be adjusted in relation to the length of the needle (since the length of the needle shaft will determine both the volume of the substance being transported therethrough) and, the needle track made so as to determine the volume of the space available for said substance to fill upon it being expressed through the needle and into the needle track and surrounding tissue. For example, a 2 mm long needle can be used for delivering substances to skin layer tissues and provide for injection of a volume in the range of 0.01 ml to 0.05 ml, while a 5 mm long needle can be used to deliver volumes in the range of 0.1 ml to 0.15 ml, and a 1.5 to 2 cm long needle can be used for delivering volumes in the range of 0.3 ml to 0.5 ml.

Other substances may also be co-transfected with the molecule of interest for a variety of beneficial reasons. For example, the molecule P199 (lee, et al. PNAS., 4524-8, 10, 89 (1992)), which is known to seal electropermeabilized membranes, may beneficially affect transfection efficiencies by increasing the survival rate of transfected muscle fibers.

Figure 6:
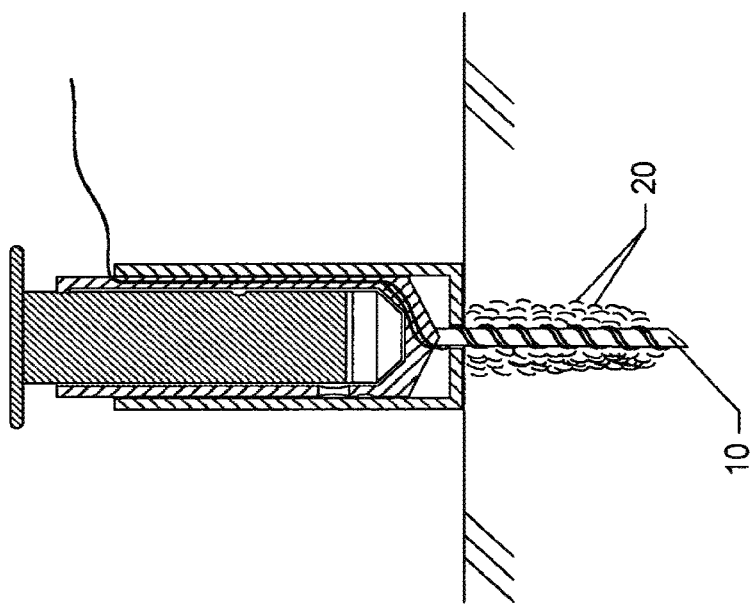
FIG. 6 shows a depiction of the invention device in use wherein during insertion or after the electrode/delivery needle is inserted into the tissue, the fluid material administered, the electrodes are energized so as to impart an electric field outward from the needle track and into the tissue. The electric field dissipates outward into the tissue from the site of the inserted needle.

With reference to FIG. 6, the electrode carrying hypodermic needle is inserted into a patient tissue to a desired depth of penetration. The plunger of the attached syringe is activated to inject the volume of liquid containing the selected material for injection, and the electrodes are immediately thereafter, or alternatively simultaneously with the injection of the material, energized with at least one pulse of electric energy sufficient to cause at least some of the cells in the treatment zone to become reversibly porated. Although the syringe plunger is typically activated using animate means, such as by use of the hand, the syringe can also be affixed to a holding device such as disclosed in FIGS. 9A-D, or even an automatic dispensing apparatus, such as a device disclosed in U.S. patent application Ser. No. 10/612,304 filed Jul. 3, 2003 which is herein incorporated in it entirety by reference.

In other embodiments, the invention can be applied to electroporation of cells at various depths from the surface of a body tissue. For example, besides electroporation of cells residing within muscle tissue compartments in which delivery of substances are initiated by injection of materials into the tissue in an orientation approximating 90 degrees from the surface of the tissue, in one embodiment the invention device can be used to electroporate cells in the subcutaneous, intradermal, or subdermal spaces of skin. It can also be used to electroporate substances into lymph nodes, or tissue layers in other organs such as cardiac and blood vessel tissue. With respect to electroporating cells in any of these locals, use of the device for electroporating cells in such tissue layers can include use of either short needles having a length sufficient for penetrating outer portions of the tissue layers (i.e., skin, subdermal, etc.) for injection and electroporation at approximately a 90 degree angle to the tissue surface, or where a delivery needle is relatively long, such as between 3 and 4 cm, insertion of the single needle can be made at an acute angle to the surface tissue using a holding device as depicted in FIGS. 9A. This will allow for electroporation of a larger portion of tissue within the desired layer. Further, the acute angle of insertion can be between 3 to 25 degrees of angle from the tissue surface. Such tissue surface can be described as forming generally a flat surface area forming a plane encompassing the site for insertion of the single needle/electrode. As depicted in FIG. 9A to D, the syringe can be connected to an attachment means which is designed to hold the syringe at a set angle on a planar guide tray 100 with the needle placed a set distance X into the tissue as determined based on the predetermined desired depth of insertion of the needle into the tissue. The guide tray with exposed needle is brought into contact with the tissue surface such that the needle inserts the tissue at the prescribed acute angle. After the needle is so inserted and the therapeutic substance expelled from the syringe, the electrodes can be energized to bring about delivery of the injected material into the subcutaneous, intradermal, or subdermal cells. Use of the device at an oblique angle as discussed above can also apply to electroporating various layers of organ tissue.

EXAMPLES

The following examples are given to illustrate various embodiments which have been made of the present invention. It is to be understood that the following examples are not comprehensive or exhaustive of the many types of embodiments which can be prepared in accordance with the present invention.

Example I

Figure 5C:
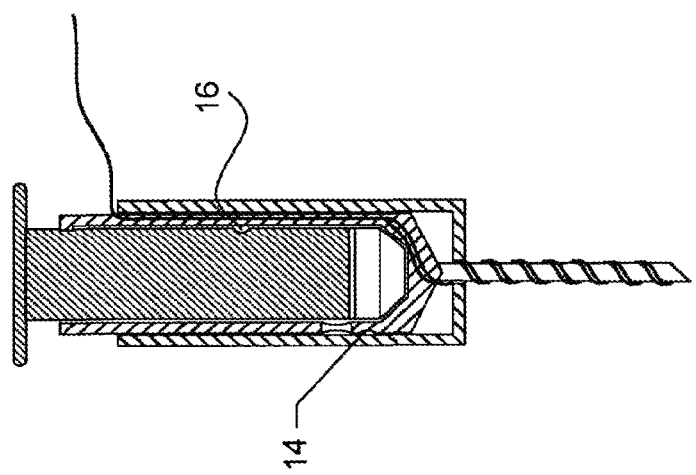
FIGS. 5A-C depict one embodiment of the invention wherein the invention electrode is shown comprising further embodiments including a reservoir, typically a syringe styled reservoir, and a sharps cover which is capable of retracting as the needle is inserted into a patient tissue. These drawings also show other features that can be embodied within the invention device such as a resilient membrane which can be pierced such as by a needle to fill the reservoir and mechanisms for allowing the sharps cover and the syringe plunger to be held in place either in an extended or retracted position. Moreover, the retractable sharps cover also act as a needle guide and can be fitted with stops to act as a depth guide. Although not shown, the single needle electrode can be fitted to a syringe and attached to an automatic needle delivery/simultaneous fluid delivery electroporation device such as that depicted in U.S. patent application Ser. No. 10/612,304 and PCT/GB2003/002887. In such embodiment, the device would only have one needle and one syringe.
Figure 5B:
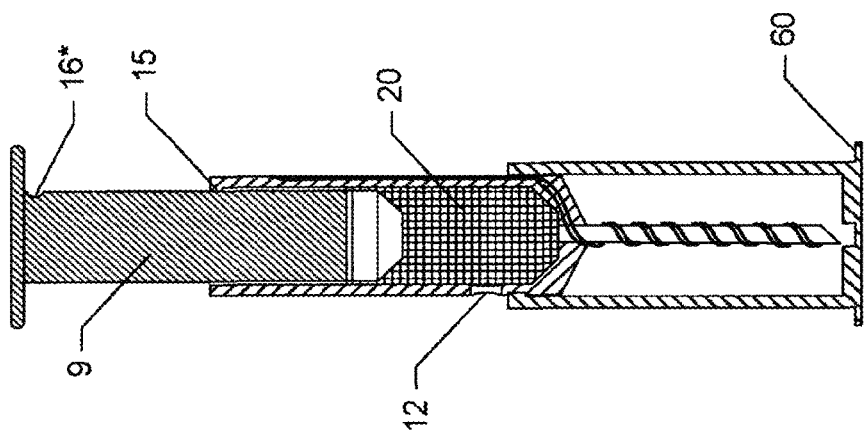
Figure 5A:
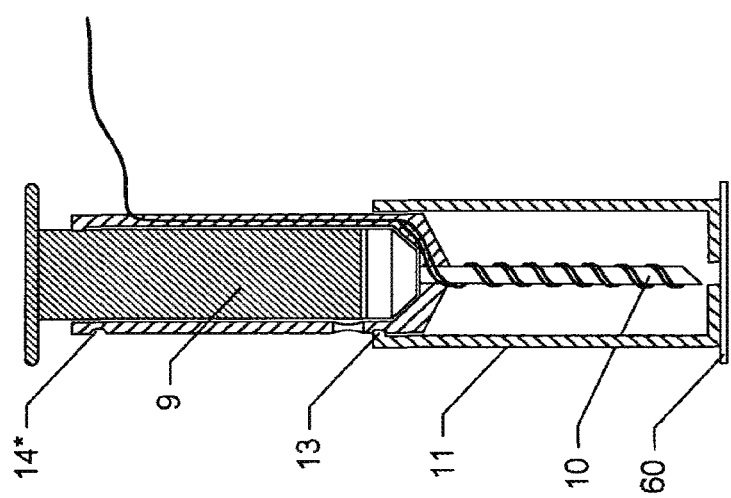

Turning now to various aspects of the invention, the device can comprise molecule delivery reservoir 20 and electrode needle 10 components as shown for example in FIGS. 5A-C. Additional embodiments include sharps cover 11, resilient membrane 12 sealing a portion of the structure comprising the reservoir 20 for uses in filling the reservoir (such as by piercing of a syringe needle), and mechanisms such as dimples 13 and recesses 14 and 14* in the reservoir 20 housing structure for keeping the sharps cover 11 in a semi fixed position of either open/retracted (FIG. 5C), or closed/covered (FIGS. 5A and B). Further embodiments include mechanisms for keeping the plunger 9 in a semi fixed open/retracted or a closed/expelled position, such as, for example, dimples 15 and recesses 16 and 16*. It should be clear to one of skill in the art that regardless of the method employed to provide for semi fixed positioning of the sharps cover 11 and plunger 9, such positioning can easily be changed with either animate energy, such as force by hand, or mechanically, such as by an electronically driven actuator. The distal end of the sharps cover 11 can include removably attached thereto a sterility cover 60. The electrode needle 10 further can comprise a lumen running therethrough ending in tissue piercing tip 22, and orifice 25 for connecting to the reservoir 20 (See FIG. 1). The needle 10 can have a length running from one end of the needle 27 to the tip 22 at the other end of the needle. The injection needle 10 can be of a gage between 18 and 29 standard hypodermic needle gauge sizes. In a preferred embodiment, the delivery needle comprises at least one pair of electrodes, such as electrodes 21a and 21b of FIG. 1. The electrodes comprise at least one anode and one cathode electrodes which are in electrical communication with electrode leads 24a and 24b. Depending upon the design chosen for any particular invention product, the leads can terminate in a lead terminal 23 (see FIGS. 3A and 4, for example), or connect by any other means with lead wires running from the electrode to a source of electrical energy, such as a pulse generator. The needle component 10 can further include a connector 26 (FIGS. 3A and 4) for attaching to a hypodermic syringe reservoir, or to a syringe reservoir affixed with a locking mechanism to detachably fasten the needle component 10 to a hypodermic syringe port.

In further embodiments, the reservoir 20 can be manufactured with a predetermined substance for treating a particular condition. Alternatively, the reservoir can be filled with a substance of interest by either drawing such substance into the reservoir through the electrode needle 10 by extracting the plunger 9, or preferably, the reservoir can first be cleared of the plunger by retracting the plunger to the open position followed by delivering to the reservoir the substance by injecting it into the reservoir via the resilient seal 12, similarly to the procedure commonly performed in the extracting of drugs from sterile vials into syringes and introducing them into another reservoir.

Figure 7:
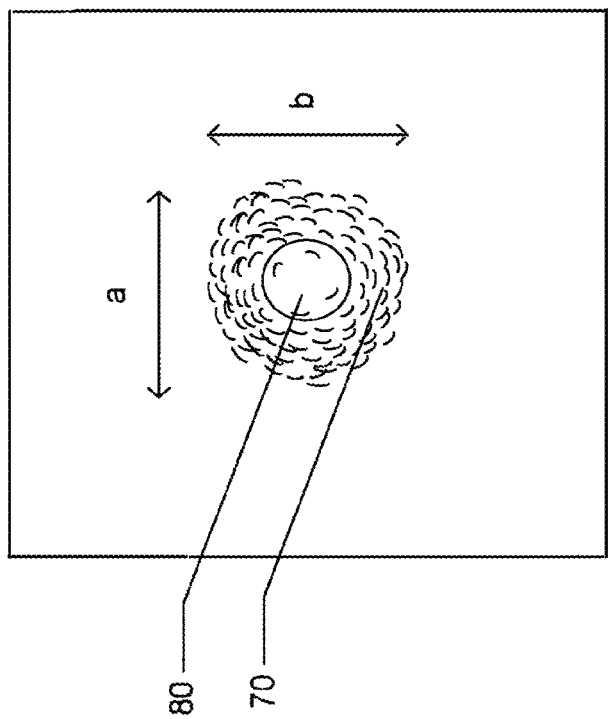
FIG. 7 shows a top view of a hypothetical tissue and a depiction of typical electric field that the invention device would generate in the tissue surrounding the needle track and having lateral dimensions (a) and (b).

The delivery needle 10 with its array of electrodes (such as electrodes 21a and b, 31a and b, 51a and b and 52a and b, or 41 and 42, FIGS. 1-4, respectively) can be inserted into the tissue, usually at an approximate 90 degrees to the tissue surface, or alternatively at an acute angle with respect to the tissue surface, and the substance injected into the needle track and local tissues. The electrodes can be energized using a pulse generator either following the injection of said substance, or can be energized simultaneously with said injection of substance. As depicted in FIG. 6, when energized with an electric pulse, the electrodes support the generation of an electric field 20 that provides for sufficient energy to cause reversible poration of the cells within said field. The electric filed generated is non-uniform in that it exponentially decreases by the distance from the needle track 80 (FIG. 7). Thus, the electric field sufficient to provide such poration has, depending upon the energy employed, symmetrical lateral dimensions (a) x (b) (shown in FIG. 7) forming a set diameter of an electroporating electric field which, with respect to the needle track length, forms a defined three dimensional volume. Generally, the poration sufficient electric field has a radius from the electrode needle 10 of between 0 and 5 mm, typically between 0 and 4 mm, and preferably between 0 and 3 mm and most preferably between 0 and 2 mm.

Figure 8C:
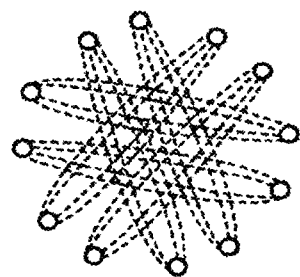
FIGS. 8A-C are drawings showing prior art arrays with typically relatively uniform lines of force and corresponding electric fields between array needles as opposed to that of the invention wherein a non-uniform lines of force and respective electric field surrounds the array and dissipates rapidly therefrom. For example.
Figure 8B:
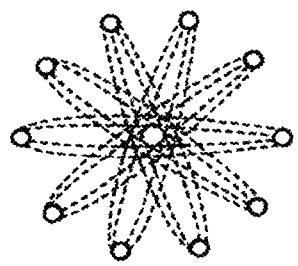
Figure 8A:
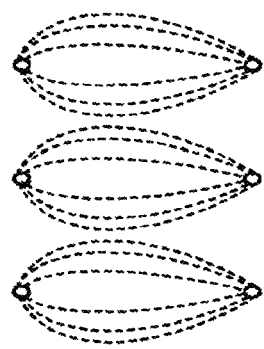

As is easily understood by those having skill in the electroporation arts, the field generated by the current invention's single needle electrode, unlike prior electroporation apparatuses, is a non-uniform electric field wherein the field intensity is greater near the needle and diminishes as measured outward from the electrodes In contrast to the current electrode arrangement, FIGS. 8A-C depicts prior electrode arrangements wherein a uniform electric filed is employed across a large volume treatment site. The instant invention is measurably distinct from former concepts that suggested a need to utilize a "uniform" field. Here, the invention employs a non-uniform field which provides for reversible poration of cells to a greater amount near the position of the delivery needle, i.e., the needle tract. This in turn allows a clear benefit to determine the precise location of those cells receiving a known dose of therapeutic materials. This invention through its embodiments therefore provides for "fitting" the electric field to the injection site so as to distribute material to cells more uniformly and confined to a local tissue area as opposed to the variable distribution allowed for with electroporation systems that use a conventional uniform electric field and an outer array of electrodes.

With respect to the electrodes generally, they can comprise any metal but preferably are a metal that does not impart a toxicity due to metal ions to the cells of the electroporated tissue. Such materials include gold, tungsten, titanium nitride, platinum, platinum iridium, and iridium oxide. The electrode material can be formed on the delivery tube (i.e., injection needle) such that there is a layer of insulation between the electrodes and the delivery tube as suggested in FIG. 3B. Alternatively, the needle can comprise a material that is nonconductive itself eliminating a specific need to insulate the electrodes from the injection tube. In this aspect, the delivery tube can be constructed from any suitable material for insertion into tissue in situ that is non-conductive, including, such as a ceramic, or hardened biocompatible plastic, including polyvinylchlorine or the like.

Figure 10B:
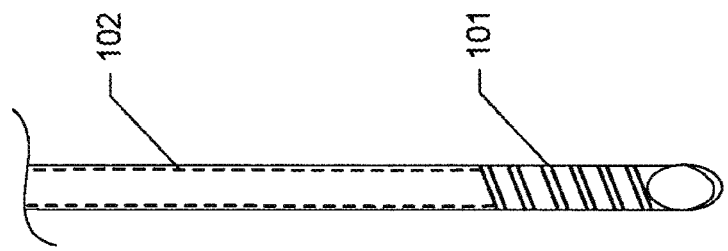
FIG. 10B depicts a needle supporting spiral electrodes. The leads for each of the positive and negative anodes are depicted running up an internal section of the needle. Also, this depiction in each of FIGS. 10A and 10B is intended to represent that the upper portion of the elongate needles can comprise insulation either around the electrode leads and/or coating the upper needle shaft.
Figure 10A:
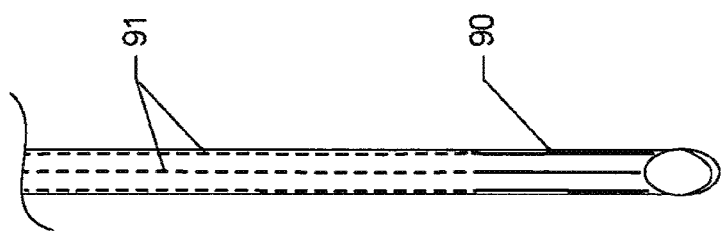
FIGS. 10A and B show partial views of delivery needles comprising electrodes exposed near the tip of the delivery needle.

In a further embodiment, the delivery needle/electrode component can be designed such that the electrodes 90 or 101 (FIGS. 10A and B) are exposed for electroporation only near the tip of the needle as depicted in FIGS. 9A, and 10A and B. The unexposed portions 91 and 102 of the electrodes can be insulated and run along the delivery needle exterior or internal to the needle. Specifically, where it is desired to position the defined treatment volume (defined by the dimensions of the electroporation electric field imparted to the tissue by the electrode array) in a particular tissue, with the intent of avoiding electroporation of other tissues, electrodes, such as disclosed in FIGS. 10A and B, can be used, for example, to electroporate deep muscle tissue and avoid other tissues lying closer to the tissue surface, such as fat cell layers, or alternatively to electroporate tissues near the surface, such as for example, subdermal tissues, as suggested in FIG. 9A. Such embodiments provide for additional control over placement and size of the treatment volume.

Example II

In this example, results are depicted for delivering molecules by reversible poration to cells situated along and near the track formed by the insertion of the invention single hypodermic needle electrode into a tissue.

Figure 11A:
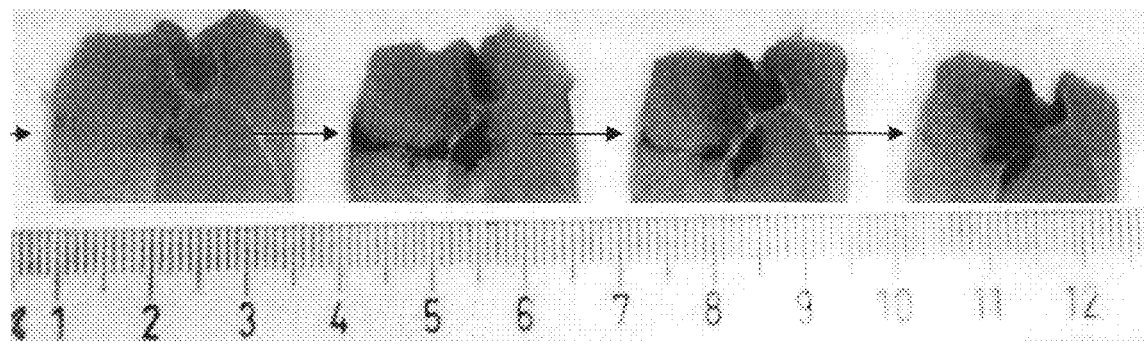
FIGS. 11A and B show results of electroporation in a tissue wherein cells primarily near the needle track have been affected by poration.
Figure 11B:
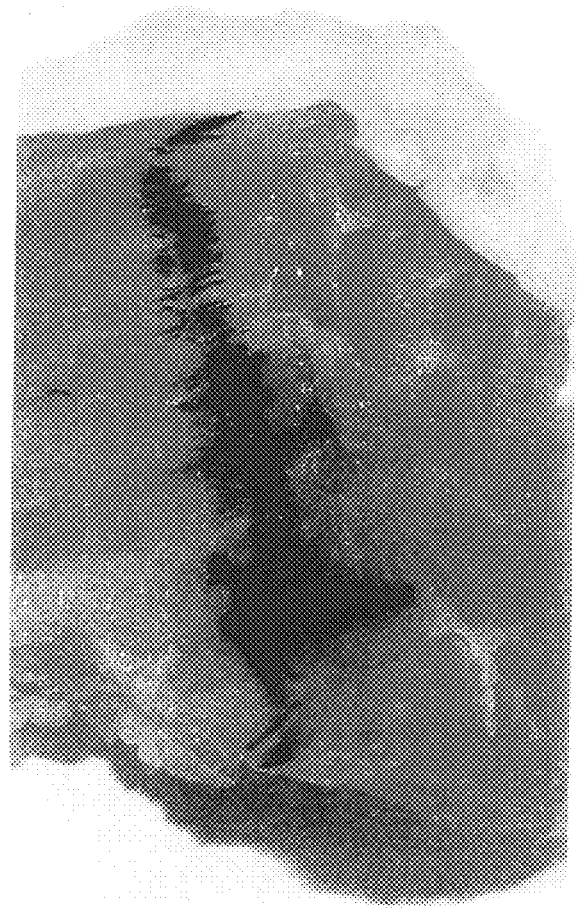
FIG. 11B shows a close-up of a central slice directly along the needle track.

As depicted in FIGS. 11A and B, rabbit quadriceps muscle was injected with DNA encoding beta-galactosidase in a bolus comprising 0.2 ml and concentration of 1 mg/ml. The electrodes were pulsed using 2 pulses of 250 mAmps, 20 millisec duration. Following electroporation, the beta-galactosidase gene was expressed in cells affected by the electroporation. At day 4 after electroporation, the rabbits were sacrificed and the muscles were prepared in 3 mm thick slices through the site on insertion of the single needle/electrode. Following chemical fixation, the beta galactosidase expressing cells in the muscle slices where visualized by an enzymatic reaction. The arrows in FIG. 11A depict the direction of the insertion of the delivery tube into the rabbit muscle. As shown, staining occurs predominantly along the track formed by insertion into the tissue of the needle delivery electrode.

Example III

Figure 12:
FIG. 12 shows the results of a single injection into rabbit high muscle of a nucleic acid containing an expression vector encoding a fluorescent marker protein (GFP) using an electroporation device according to the invention.
Figure 13A:
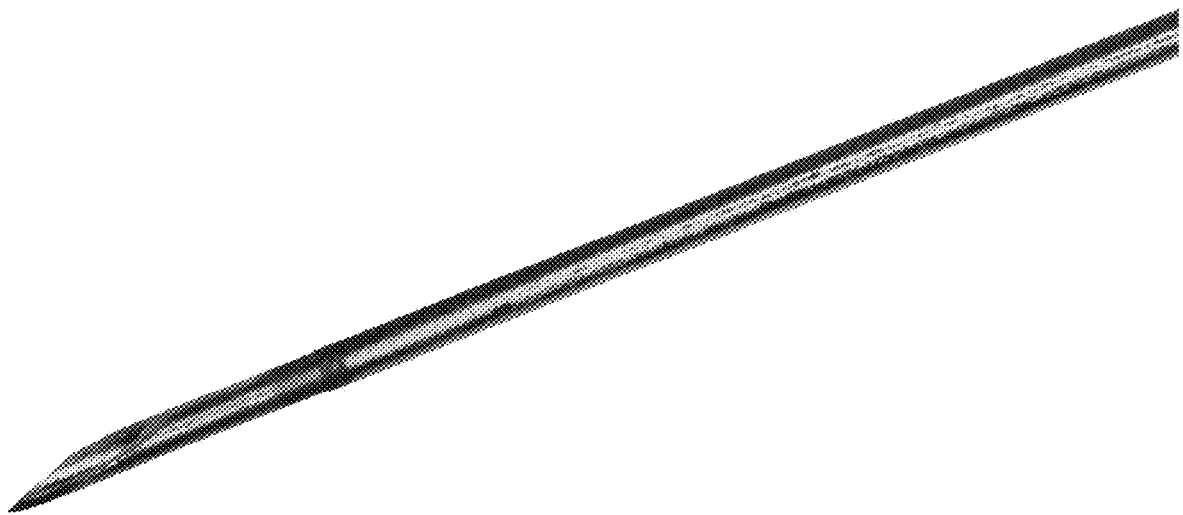
FIGS. 13A, B, C, D, and E show magnified photographs of a prototype hypodermic needle wherein gold elongate electrodes have been etched onto a standard injection needle using MEMS technology, i.e., micro layering, and etching and relayering of materials onto the base injection needle shaft such that the electrodes comprise ¼ of the needle shaft circumference each.
Figure 13B:
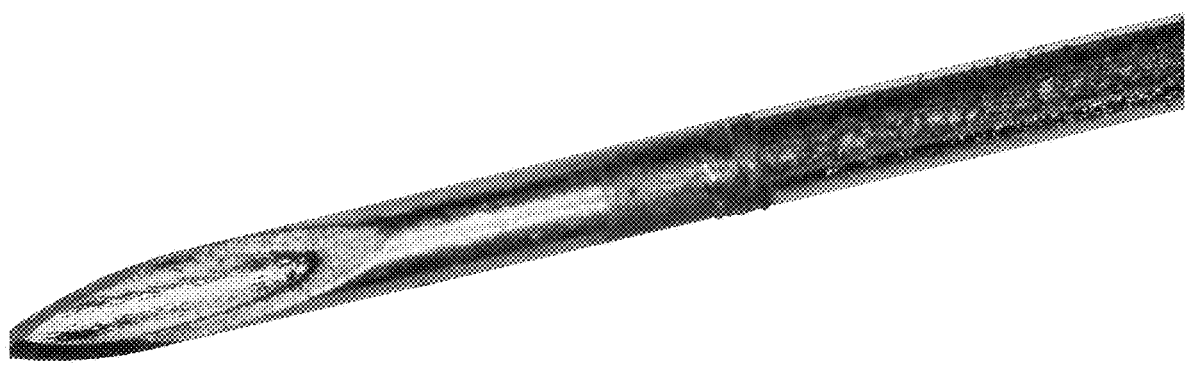
In FIG. 13B, a detail photo is shown from an angle allowing visualization of the terminal sections of both gold electrodes.
Figure 13C:
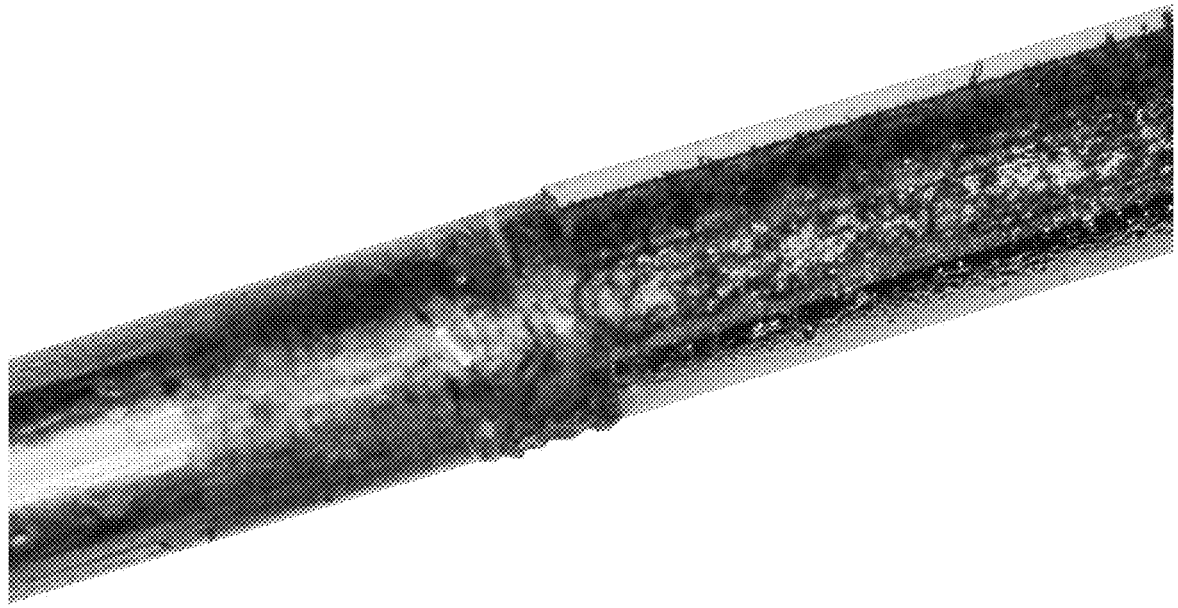
FIG. 13C is another perspective showing detail of the terminal sections of the electrodes etched onto the needle shaft.
Figure 13D:
FIGS. 13D and E show another embodiment wherein the MEMs crafted electrodes are ¹⁄₁₆ the circumference of the needle shaft.
Figure 13E:

This example describes experiments that employ an electroporation device according to embodiments of the invention to deliver DNA encoding green fluorescent protein (GFP) into rabbit quadriceps muscle, the results are shown in FIG. 12.

Here, several New Zealand white male rabbits, each weighing 4-5 kg (Perry Scientific, San Diego, Calif.), were each injected with an expression vector (gWizGFP, lot 12311, purchased from Aldevron, LLC, Fargo, N. Dak.; see also Gene Therapy Systems, Inc., San Diego, Calif.) encoding a bright GFP (Cheng, et al. (1996), Nature biotechnology, vol. 14:606-9) the expression of which was under the control of a modified human cytomegalovirus immediate early promoter/enhancer.

Figure 1:
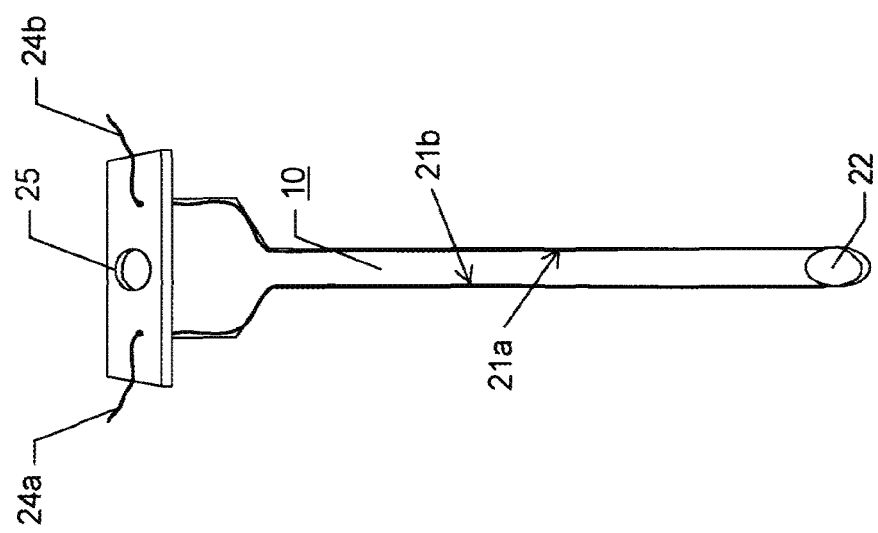
FIG. 1 is a drawing depicting a hypodermic needle with elongate electrodes integrated therein. The needle features a port for dispensing a liquid formulation from a lumen running there through, and a port for connecting to a fluid carrying reservoir.

Prior to injection, each rabbit was first sedated with acepromazine (1 mg/kg) and then anesthetized by intramuscular injection of a mixture of ketamine (35 mg/kg) and xylazine (5 mg/kg) in the presence of glycopyrrolate (0.01 mg/kg), which had been previously administered subcutaneously to prevent uneven heart beating as a result of the ketamine/xylazine treatment. The rabbit was then shaved at the site where the injection was to be made, i.e., into the quadricepts muscle. A hole was poked in the skin covering the muscle by first inserting an 18 gauge needle, and then slightly widened using a scalpel. A single needle electroporation device, made from an 18 gauge needle with two parallel electrodes applied opposite one another to the outer surface of the needle (as depicted in FIG. 1), was then slowly inserted into the muscle tissue, periodically pausing to inject DNA every few millimeters to a final insertion depth of approximately 25 mm. A total of 500 ul of DNA-containing solution containing 100 ug gWizGFP was injected into each injection site. Shortly after completing the injection and while the needle/electrode device was still inserted to its final insertion depth, electroporation was commenced. Specifically, five 250 mA pulses, each of twenty millisecond (ms) duration, were applied to the electroporation needle device at 10 Hz intervals (i.e., 100 ms) using an Elgen 1000 (Inovio AS, Oslo, Norway) current-clamped pulse.

Four days post-treatment the animals were humanely euthanized. Skin covering the region of the leg where the vector was delivered was carefully removed, after which each animal was placed at −20° C. for about 1 hour. Treated muscle was then removed using a scalpel and then placed at −20° C. for another 1 to 2 hrs. The frozen muscle tissue was then sectioned into slices approximately 3 mm thick using a rotating meat slicer. Muscle slices where arranged in plastic trays and examined for GFP expression using a Leica MZ 12 dissection microscope fitted with a UV light and GFP filter combination. FIG. 12 is a representative photo of the results obtained by this analysis, and clearly shows that an electroporation device according to the invention can be used to successfully deliver an agent, for example an expression vector encoding a desired protein that is then expressed in active form, into cells.

Example IV

Figure 15:
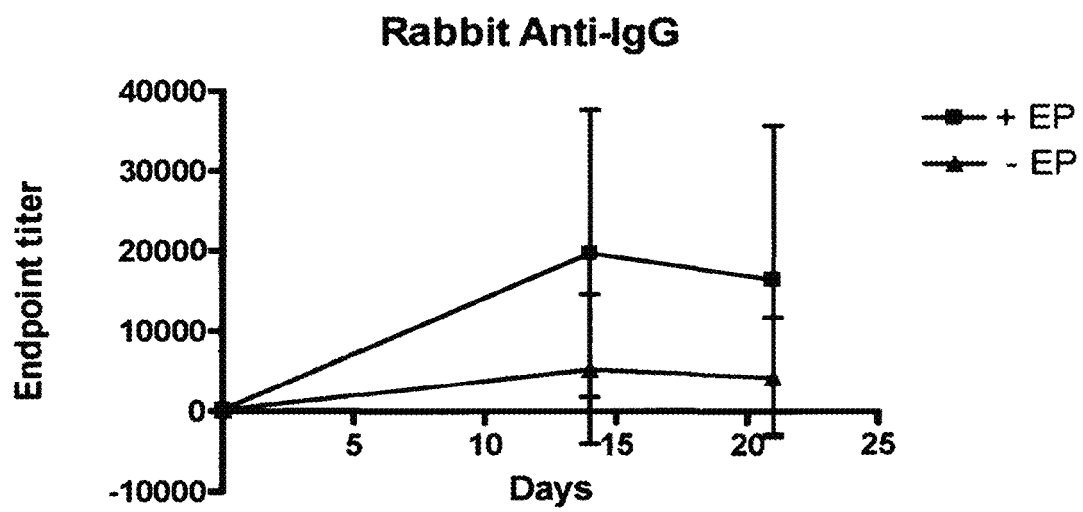
FIG. 15 is a graph showing the level of rabbit anti-human IgG antibodies produced following electroporation pulse using the single needle invention (■) versus no electroporation (▲)
Figure 16:
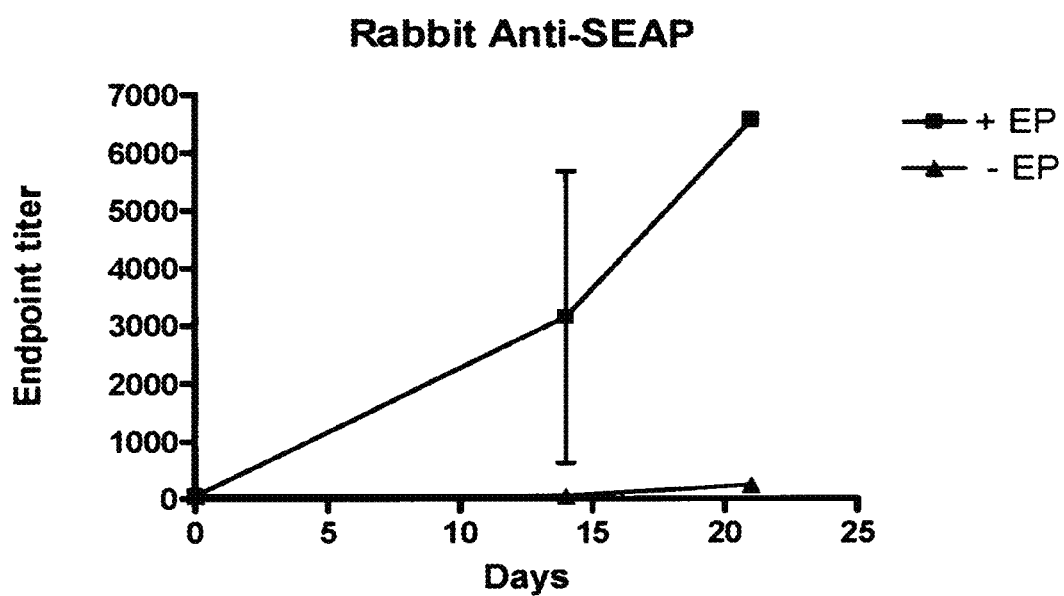
FIG. 16 is a graph showing the level of rabbit anti-SEAP antibodies produced following electroporation pulse using the single needle invention (■) versus no electroporation (▲)
Figure 18B:
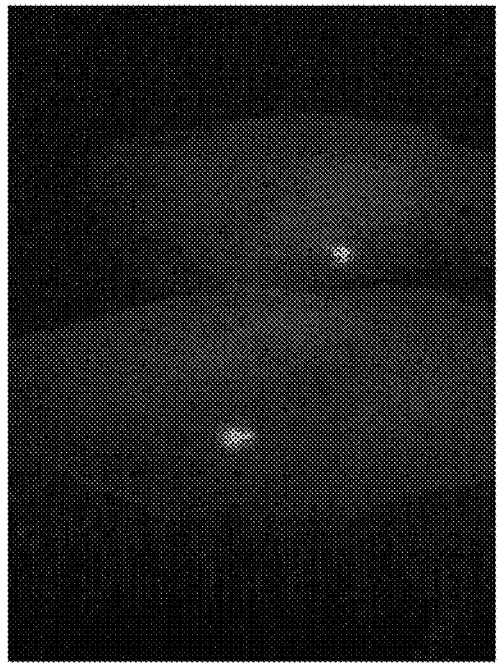
FIGS. 18A and B are photographs showing combination of natural light and green florescence, or fluorescence alone respectively, wherein injection of plasmid DNA encoding GFP was followed by electroporation carried out using a single needle electrode comprising a 23 gauge needle and anode and cathode electrodes having a width of $\frac{1}{16}$ the circumference the needle shaft. In this experiment, the electrodes were pulsed at a constant current of 50 mA.

In this example, data for which is shown in FIGS. 15 and 16, using the invention electrode configuration, plasmids encoding SEAP (pSEAP#3348, Aldevron) and IgG (pLNOH 2hg3 #11765, Aldevron) were electroporated into cells of test animal tissues (i.e., intramuscular injection into the tibialis anterior of the animal) and the expression monitored to prove success of expression in rabbit muscle as well as measuring immune responses against both a "week" and a 'strong" antigen (SEAP and IgG, respectively). In these experiments the SEAP and IgG plasmid were administered at a final concentration of 1 ug/ul.

Animals used were New Zealand White male rabbits 3.5 to 4.5 kg. Electroporation was carried out using an Elgen 1000 (Inovio AS, Oslo, Norway Serial number 009) which further comprised a current-clamped pulse generator (prototype) and a single needle prototype wherein the electrodes ran parallel to the injection track and approximately between 1 mm apart. The electrodes were pulsed for 20 millisec pulse length with 5 pulses each at 150 mA with a 250 millisec interval between pulses (i.e., a frequency of about 4 Hz). The electrodes extended into the tissue to about 1.0 cm depth.

The experiments each comprised a two-step delivery process, i.e., injection of the plasmid solution (200 ul) using a 29 gauge insuline syringe with injection during insertion of the needle to distribute DNA at different depths, followed by removal of the injector needle and insertion of the single needle electrode.

As shown in Table I below, each of the IgG and SEAP experiments had two groups of test animals, i.e., one set of animals receiving electroporation and the other not (control)

TABLE I

| Group # | Current | Treatement |
|---|---|---|
| 1 | 150-250 mA | 100 ul × 2 SEAP 1 mg/ml, 100 ul × 2 left tibialis, IgG 1 mg/ml 100 ul × 2 right tibialis |
| 2 | No EP | 100 ul × 2 SEAP 1 mg/ml, 100 ul × 2 left tibialis, IgG 1 mg/ml 100 ul × 2 right tibialis |

As indicated in Table II, three different electrode embodiments were tested, (1) a single needle electrode in which the anode and cathode electrodes were applied to a 23 gauge needle at $\frac{1}{16}$ the circumference of the needle each and applied to the full length of the needle by MEMs technology (FIGS. 13D-E), (2) a single needle electrode wherein the electrodes are $\frac{1}{4}^{th}$ the circumference of the needle shaft each (FIGS. 13A-C), and (3) a single needle arrangement wherein the electrodes are 1 mm apart without a fluid medium delivery tube. As shown in Table II, the various combinations of pulsing were performed.

The protocol used for each animal in this experiment comprised injecting the GFP plasmid at the noted concentrations, electroporating the tissue using an embodiment of the single needle electrode, followed by sacrificing of the animals and performing tissue preparation by slicing the treated muscle in adjacent slices and observing florescence. Generally, due to the difficulty of slicing the tissue so as to retrieve slices parallel to the injection track, GFP florescence in the figure photos often show up as circles or elipses. These florescence patterns prove that the single needle concept is functional and provides for electroporation of tissue a very low voltages and relative electric current in defined locations surrounding the needle track and within the tissue.

TABLE II

| Electrode design | Tissue site | Constant current | Voltage (average V) | Number of pulses | pGFP DNA concentration/volume |
|---|---|---|---|---|---|
| Electrodes ¼ shaft circumference | Quadriceps | 0.0 | 0.0 | 0.0 | 0.2 mg/ml |
| Electrodes ¹⁄₁₆ shaft circumference | Quadriceps | 50 mA | 8 | 2 | 0.2 mg/ml |
|  | Quadriceps | 100 mA | 18 | 2 | 0.2 mg/ml |
| Electrodes ¼ shaft circumference | Quadriceps | 50 mA | 11 | 2 | 0.2 mg/ml |
|  | Quadriceps | 100 mA | 15 | 2 | 0.2 mg/ml |
|  | Quadriceps | 150 mA | 20 | 2 | 0.2 mg/ml |
|  | Quadriceps | 250 mA | 33 | 2 | 0.2 mg/ml |
| Electrodes 1 mm spacing without fluid delivery embodiment | Tibialis | 75 mA | 13 | 2 | 1.0 mg/ml |
|  | Tibialis | 150 mA | 18 | 2 | 1.0 mg/ml |
|  | Tibialis | 250 mA | 28 | 2 | 1.0 mg/ml |
|  | Quadriceps | 150-200 | 20 | 2 | 1.0 mg/ml |
|  | Quadriceps | 250-500 | 40 | 2 | 1.0 mg/ml |
|  | Quadriceps | 600-1000 mA | 50 | 2 | 1.0 mg/ml |

Samples were taken Day 0, 14 and day 21. The rabbits were then terminated on day 21 with subcutaneous injection of 0.5 ml hypnorm (Hypnorm 0.1 ml/kg) followed by i.v. injection of 1 ml/kg of 10% Pentorbarbital in the ear vein.

As is clear from the results of FIGS. 15 and 16, the levels of antibody titer elicited from the single needle delivery are far in excess of the negative control. Specifically, the two test antigens (IgG and SEAP) elicited titers relative to one another as expected with IgG being a much stronger antigen that SEAP (see titer scale). Both antigens elicited antibody production in the electroporated samples and virturally no antibody production in the non-electroporated samples.

Experiment V

In this experiment, prototype MEMs manufactured single needle electrodes were tested in rabbit tissue using a variety of pulsing energies and green florescent protein expression.

Figure 17B:
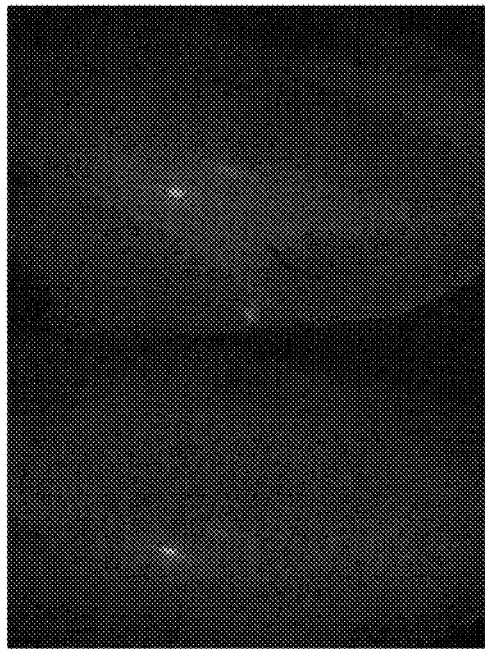
FIGS. 17 A and B are photographs showing results of green florescent protein (GFP) expression following injection of plasmid DNA encoding GFP followed by no electroporation. In combination of natural and fluorescent light.
FIG. 17A shows adjacent slices of tissue in the vicinity of the injection/needle track site. The photos show no expression without electroporation.
Figure 17A:

FIGS. 17A and B show both natural light and florescent light, respectively, photographs of GFP expression following injection of plasmid DNA encoding GFP with no electroporation. As indicated, there is virtually no green florescent protein expression. Thus, it is clear that without electroporation there is not sufficient uptake and expression of the desired gene.

Figure 18A:
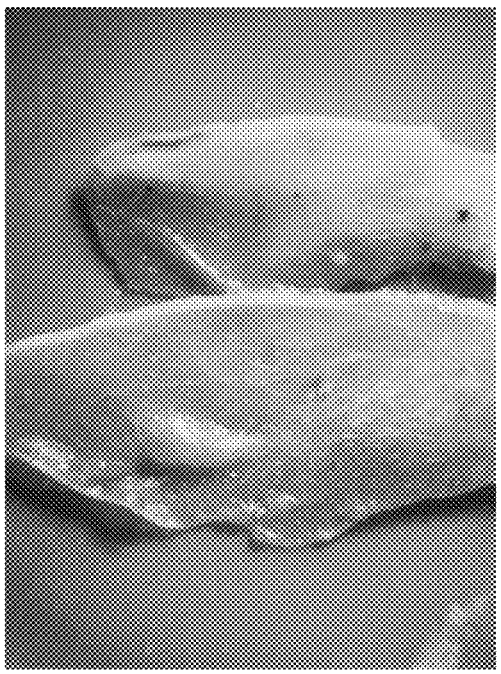
Figure 19A:
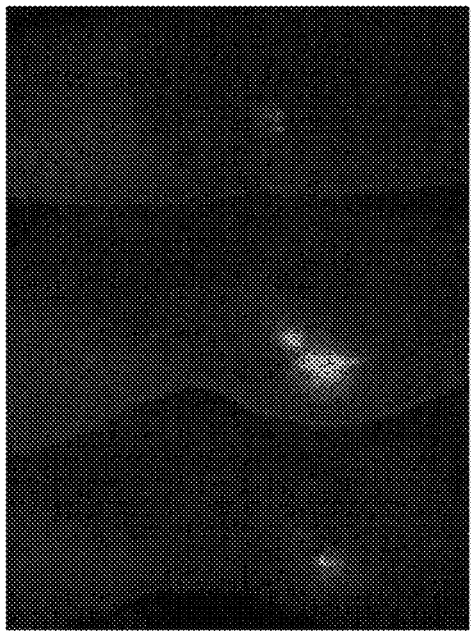
FIGS. 19A and B are photographs showing combination of natural light and green florescence or fluorescence only, wherein injection of plasmid DNA encoding GFP was followed by electroporation carried out using a single needle electrode comprising a 23 gauge needle and anode and cathode electrodes having a width of $\frac{1}{16}$ the circumference the needle shaft. In this experiment, the electrodes were pulsed at a constant current of 100 mA.

With respect to electroporation in situ using the $\frac{1}{16}$ width electrode model, the ability to express electroporated GFP is shown in FIGS. 18A and B and 19A and B. FIGS. 18A and B show GFP expression results upon electroporation with a constant current of 50 mA, while FIGS. 19A and B show electroporation at 100 mA.

Figure 20A:
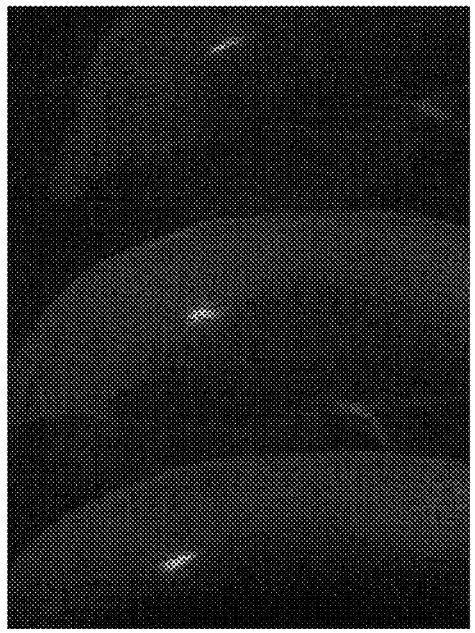
FIGS. 20A and B are photographs showing combination of natural light and green florescence or fluorescence only, wherein injection of plasmid DNA encoding GFP was followed by electroporation carried out using a single needle electrode comprising a 23 gauge needle and anode and cathode electrodes having a width of $\frac{1}{4}$ the circumference the needle shaft. In this experiment, the electrodes were pulsed at a constant current of 50 mA.
Figure 19B:
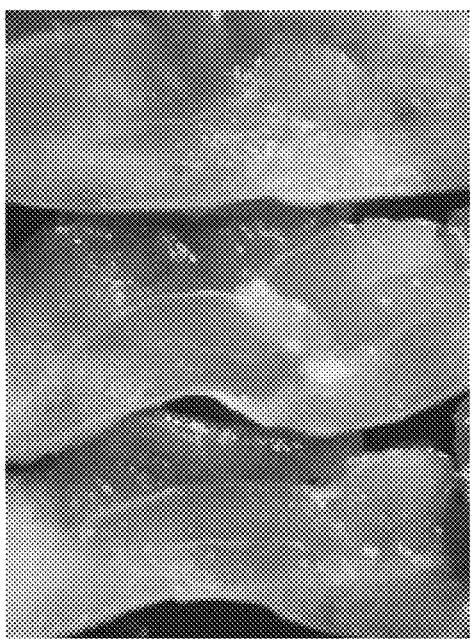
Figure 20B:
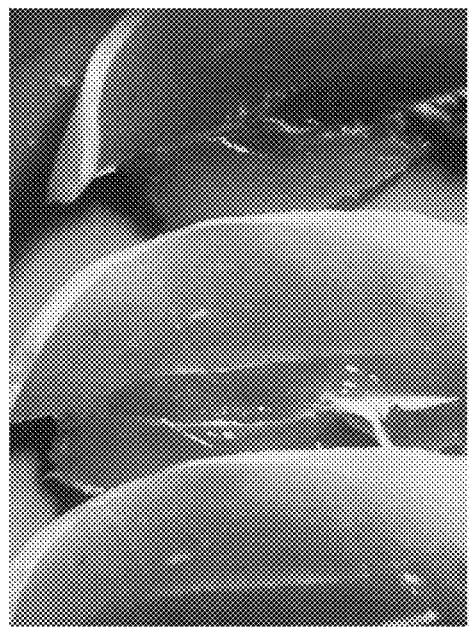
Figure 21A:
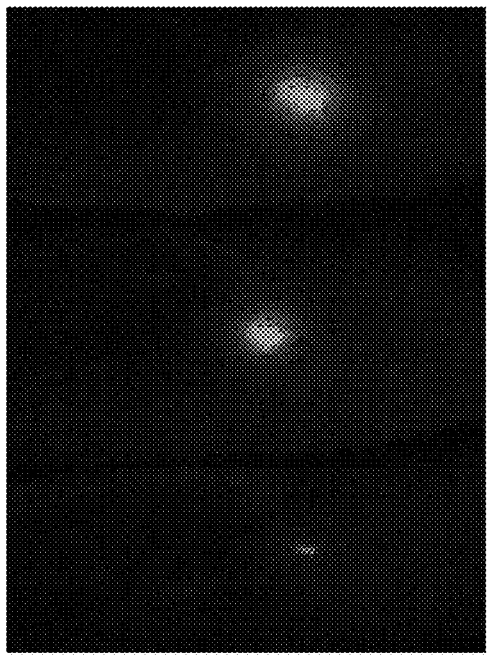
FIGS. 21A and B are photographs showing combination of natural light and green florescence or fluorescence only, wherein injection of plasmid DNA encoding GFP was followed by electroporation was carried out using a single needle electrode comprising a 23 gauge needle and anode and cathode electrodes having a width of $\frac{1}{4}$ the circumference the needle shaft. In this experiment, the electrodes were pulsed at a constant current of 100 mA.
Figure 21B:
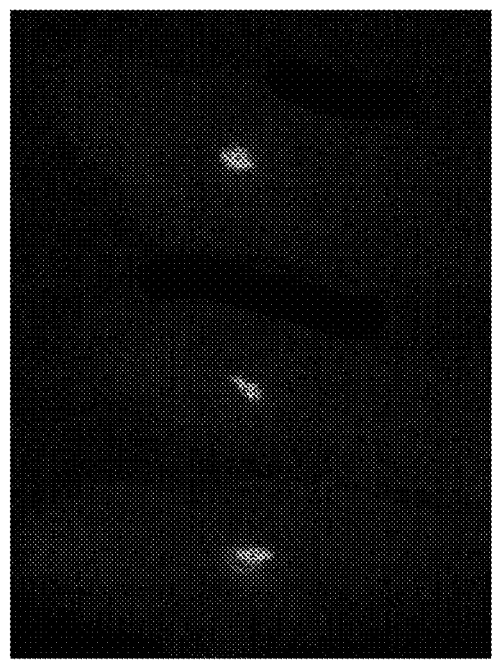
Figure 22A:
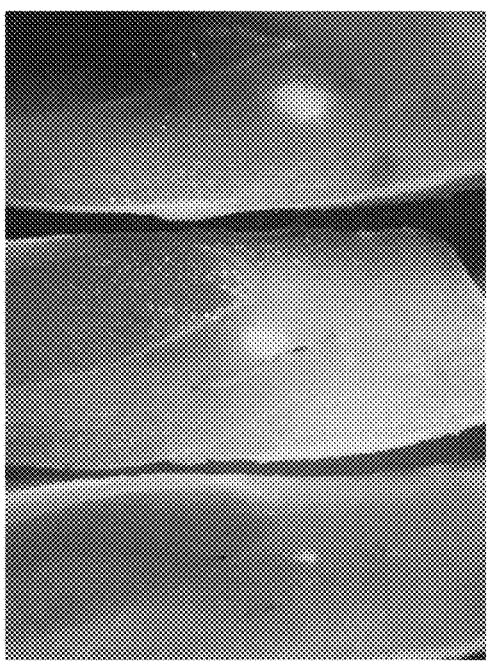
FIGS. 22A and B are photographs showing combination of natural light and green florescence or fluorescence only, wherein injection of plasmid DNA encoding GFP was followed by electroporation was carried out using a single needle electrode comprising a 23 gauge needle and anode and cathode electrodes having a width of $\frac{1}{4}$ the circumference the needle shaft. In this experiment, the electrodes were pulsed at a constant current of 150 mA.
Figure 22B:
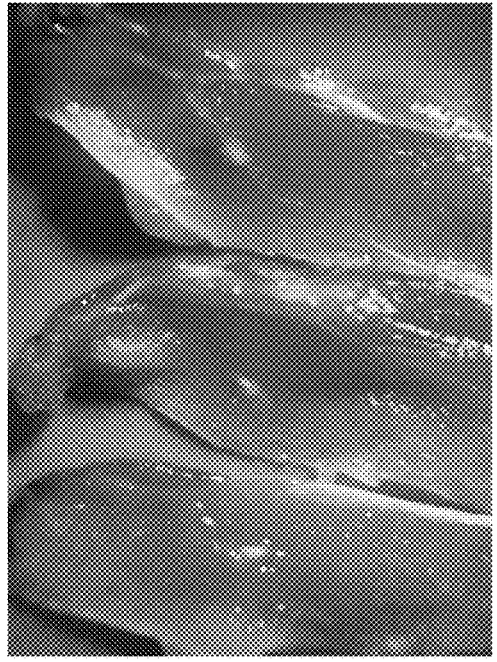
Figure 24B:
FIGS. 24A and B are photographs showing combination of natural light and green florescence or fluorescence only, respectively, wherein injection of plasmid DNA encoding GFP was followed by electroporation was carried out using a single needle electrode comprising electrodes 1 mm spacing without fluid delivery embodiment. In this experiment, the electrodes were pulsed at a constant current of 150 mA.

For GFP expression using the ¼ circumference single needle electrode, results are provided in FIGS. 20A and B, 21A and B, and 22A and B, wherein electoporation was carried out using 50, 100, and 150 mA, respectively.

Figure 23B:
FIGS. 23A and B are photographs showing combination of natural light and green florescence or fluorescence only, respectively, wherein injection of plasmid DNA encoding GFP was followed by electroporation was carried out using a single needle electrode comprising electrodes 1 mm spacing without fluid delivery embodiment. In this experiment, the electrodes were pulsed at a constant current of 75 mA.
Figure 23A:
Figure 24A:
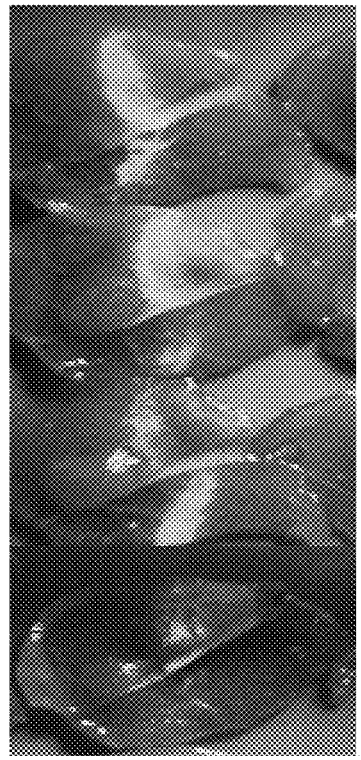
Figure 25B:
FIGS. 25A and B are photographs showing combination of natural light and green florescence or fluorescence only, respectively, wherein injection of plasmid DNA encoding GFP was followed by electroporation was carried out using a single needle electrode comprising electrodes 1 mm spacing without fluid delivery embodiment. In this experiment, the electrodes were pulsed at a constant current of 250 mA.
Figure 25A:
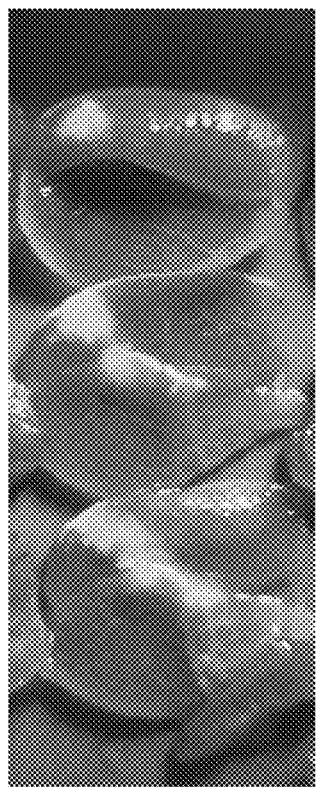

GFP expression was also testing using an embodiment wherein the single needle electrode did not comprise a fluid delivery tube associated with the electrodes. As shown in FIGS. 23A and B, 24A and B, and 25A and B, this invention device embodiment was tested at 75, 150, and 250 mA each at constant current. Here, the amount of GFP plasmid was five times the concentration of the experiments shown in FIGS. 19A-22B. Consequently, the treatment zone appears more readily.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. More specifically, the described embodiments are to be considered in all respects only as illustrative and not restrictive. All similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that use of such terms and expressions imply excluding any equivalents of the features shown and described in whole or in part thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed:

1. A method of electroporating cells in vivo, comprising:
   piercing tissue with the tip of an injection needle;
   injecting a fluid composition from a reservoir and through a hollow shaft of the injection needle, the shaft having a length extending from a proximal end of the needle to the tip, and at least two electrodes exposed along an outer surface of the shaft along at least a portion of the length, wherein the at least two electrodes are electrically isolated from one another and situated spiraling and parallel to one another along the outer surface; and
   activating an electrical energy source in electrical communication with each of the at least two electrodes, thereby providing a pulse of electrical energy that has a current in a range of 1 mAmp to 400 mAmp to the at least two electrodes causing reversible poration of the cells for their uptake of the fluid composition.

2. The method of claim 1 wherein the composition comprises a drug, a nucleic acid, an antigen, a nucleic acid encoding an expressible antigen, or a nucleic acid encoding an expressible immune modulating molecule.

3. The method of claim 1 wherein the cells comprise in situ patient cells that are subcutaneous cells, intradermal, subdermal cells, skeletal muscle cells, striated muscle cells, smooth muscle cells, organ cells, breast tissue cells, pancreas cells, spleen cells, heart cells, liver cells, or mucosal cells.

4. The method of claim 1 wherein the at least two electrodes comprise an anode and a cathode each comprising gold and/or titanium.

5. The method of claim 1 wherein the tissue is located on a patient thigh, arm, or torso.

6. The method of claim 1 wherein the composition comprises a total volume of 0.01 ul, 50 ul, 100 ul, 150 ul, 200 ul, 250 ul, 300 ul, 400 ul, or 500 ul.

7. The method of claim 1 wherein the composition comprises a total active ingredient concentration of 2 mg/ml to 3 mg/ml.

8. The method of claim 1 wherein the injecting step occurs before and/or during the activating step.

9. The method of claim 1 wherein the electrical energy source comprises a generator, and the activating step comprises supplying pulses of electrical energy at a nominal voltage per pulse between 1 and 200 V.

10. The method of claim 1 wherein the current is constant.

11. The method of claim 2 wherein the immune modulating molecule is a cytokine or a chemokine.

12. The method of claim 2 wherein the immune modulating molecule is IL-1, IL-2, IL-3, IL-4, IL-5, IL-6, IL-7, IL-8, IL-9, IL-10, IL-11, IL-12, GM-CSF, M-CSF, G-CSF, LIF, LT, TGF-E, IFN, TNF-a, BCGF, CD2, or ICAM.

13. The method of claim 9 wherein the supplying step comprises supplying the pulses of electrical energy at a frequency in a range from 1 to 10,000 Hz.

14. The method of claim 9 wherein the supplying step comprises supplying the pulses of electrical energy for a time length between about 0.1 ms to 1000 ms.

15. The method of claim 10 wherein the constant current is within the range of 10 to 40, 25 to 100, 50 to 150, 125 to 200, 175 to 250, 225 to 300, 250 to 300, and 300 to 400 mAmps.

* * * * *